US00PP20523P2

(12) United States Plant Patent
Takamura et al.

(10) Patent No.: US PP20,523 P2
(45) Date of Patent: Dec. 1, 2009

(54) ***CATHARANTHUS* PLANT NAMED 'SUNNICHIPINK'**

(50) Latin Name: *Catharanthus roseus*
Varietal Denomination: Sunnichipink

(75) Inventors: Naoto Takamura, Yamanashi (JP); Kiyoshi Miyazaki, Shiga (JP); Takuro Ishihara, Tokyo (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/217,749

(22) Filed: Jul. 7, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H. Para

*Assistant Examiner*—Louanne C Krawczewicz Myers

(74) *Attorney, Agent, or Firm*—C. A. Whealy

(57) ABSTRACT

A new and distinct cultivar of *Catharanthus* plant named 'Sunnichipink', characterized by its trailing plant habit; vigorous growth habit; freely branching habit; freely flowering habit; long flowering period; large light red purple-colored flowers with darker red purple-colored centers; and good garden performance.

1 Drawing Sheet

Botanical designation: *Catharanthus roseus.*
Cultivar denomination: 'Sunnichipink'.

RELATED TO CLOSELY-RELATED APPLICATIONS

Title: *Catharanthus* Plant Named 'Sunnichiroro'.
Applicants: Naoto Takamura, Kiyoshi Miyazaki & Takuro Ishihara.
Filed: Concurrently with this application.

BACKGROUND OF THE INVENTION

The present invention relates to a new and distinct cultivar of *Catharanthus,* botanically known as *Catharanthus roseus* and hereinafter referred to by the name 'Sunnichipink'.

The new *Catharanthus* is a product of a planned breeding program conducted by the Inventors in Higashiormi, Shiga, Japan. The objective of the breeding program is to develop new freely branching and flowering *Catharanthus* cultivars with trailing plant habit and attractive and unique flower coloration.

The new *Catharanthus* originated from a cross-pollination conducted by the Inventors in Higashiomi, Shiga, Japan in 2003 of a proprietary selection of *Catharanthus roseus* identified as code number 03CAT-7, not patented, as the female, or seed, parent with a proprietary selection of *Catharanthus roseus* identified as code number 03CAT-YM, not patented, as the male, or pollen, parent. The new *Catharanthus* was discovered and selected by the Inventors as a flowering plant from within the progeny of the stated cross-pollination in a controlled greenhouse environment in Higashiomi, Shiga, Japan in 2004.

Asexual reproduction of the new *Catharanthus* by vegetative cuttings in a controlled greenhouse environment in Higashiormi, Shiga, Japan since 2004, has shown that the unique features of this new *Catharanthus* are stable and reproduced true to type in successive generations.

SUMMARY OF THE INVENTION

The new *Catharanthus* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunnichipink'. These characteristics in combination distinguish 'Sunnichipink' as a new and distinct cultivar of *Catharanthus:*

1. Trailing plant habit.
2. Vigorous growth habit.
3. Freely branching habit.
4. Freely flowering habit.
5. Long flowering period.
6. Large light red purple-colored flowers with darker red purple-colored centers.
7. Good garden performance.

Plants of the new *Catharanthus* can be compared to plants of the female parent selection. Plants of the new *Catharanthus* differ from plants of the female parent selection in the following characteristics:

1. Plants of the new *Catharanthus* are more vigorous than plants of the female parent selection.
2. Plants of the new *Catharanthus* have light red purple-colored flowers whereas plants of the female parent selection have white-colored flowers.

Plants of the new *Catharanthus* can be compared to plants of the male parent selection. Plants of the new *Catharanthus* differ from plants of the male parent selection in the following characteristics:

1. Plants of the new *Catharanthus* are more trailing than and not as upright as plants of the male parent selection.
2. Plants of the new *Catharanthus* have light red purple-colored flowers whereas plants of the male parent selection have white-colored flowers.

Plants of the new *Catharanthus* can be compared to plants of the *Catharanthus roseus* 'Sunnichiroro', disclosed in a U.S. Plant Patent application Ser. No. 12/217,748, filed concurrently. Plants of the new *Catharanthus* differ from plants of 'Sunnichiroro' in the following characteristics:

1. Plants of the new *Catharanthus* are slightly smaller than plants of 'Sunnichiroro'.
2. Plants of the new *Catharanthus* are not as freely branching as plants of 'Sunnichiroro'.
3. Plants of the new *Catharanthus* have lighter red purple-coloredflowers than plants of 'Sunnichiroro'.

Plants of the new *Catharanthus* can also be compared to plants of 'Frappe Orange', not patented. In side-by-side comparisons conducted in Higashiomi, Shiga, Japan, plants of the new *Catharanthus* and 'Frappe Orange' differed in the following characteristics:

1. Plants of the new *Catharanthus* were taller than plants of 'Frappe Orange'.
2. Plants of the new *Catharanthus* were more freely branching than plants of 'Frappe Orange'.
3. Plants of the new *Catharanthus* had narrower leaves than plants of 'Frappe Orange'.
4. Plants of the new *Catharanthus* had larger flowers than plants of 'Frappe Orange'.
5. Plants of the new *Catharanthus* and 'Frappe Orange' differed in flower color as plants of 'Frappe Orange' had light pink-colored flowers.

BRIEF DESCRIPTION OF THE PHOTOGRAPHS

The accompanying colored photographs illustrate the overall appearance of the new *Catharanthus*, showing the colors as true as it is reasonably possible to obtain in colored reproductions of this type. Colors in the photographs may differ slightly from the color values cited in the detailed botanical description which accurately describe the colors of the new *Catharanthus*.

The photograph at the top of the sheet comprises a side perspective view of a typical flowering plant of 'Sunnichipink' grown in a container.

The photograph at the bottom of the sheet comprises a close-up view of typical flowers and leaves of 'Sunnichipink'.

DETAILED BOTANICAL DESCRIPTION

The aforementioned photographs and following observations, measurements and values describe plants grown in 13 cm containers in Higashiomi, Shiga, Japan, under commercial practice during the summer in an outdoor nursery. During the production of the plants, day temperatures averaged 25° C. and night temperatures averaged 15° C. Plants used for the description had been growing for four months. Plants used for the photographs had been growing for six months. In the following description, color references are made to The Royal Horticultural Society Colour Chart, 2001 Edition, except where general terms of ordinary dictionary significance are used.

Botanical classification: *Catharanthus roseus* 'Sunimchipink'.

Parentage:

*Female, or seed, parent.*—Proprietary selection of *Catharanthus roseus* identified as code number 03CAT-7, not patented.

*Male, or pollen, parent.*—Proprietary selection of *Catharanthus roseus* identified as code number 03CAT-YM, not patented.

Propagation:

*Type.*—By vegetative cuttings.

*Time to initiate roots, summer.*—About two weeks at 30° C.

*Time to initiate roots, winter.*—About three weeks at 25° C.

*Time to produce a rooted young plant, summer.*—About five weeks at 30° C.

*Time to produce a rooted young plant, winter.*—About six weeks at 25° C.

*Root description.*—Fibrous; white in color.

*Rooting habit.*—Freely branching; moderately dense.

Plant description:

*Plant and growth habit.*—Trailing plant habit. Freely branching with about 13 primary lateral branches developing per plant. Vigorous growth habit.

*Plant height.*—About 16.4 cm.

*Plant diameter.*—About 35.5 cm.

Lateral branch description:

*Length.*—About 20.9 cm.

*Diameter.*—About 2.4 mm.

*Internode length.*—About 1.7 cm.

*Strength.*—Strong.

*Aspect.*—Upright to outward.

*Texture.*—Pubescent.

*Color.*—Close to 145C.

Foliage description:

*Arrangement.*—Opposite, simple.

*Length.*—About 5.8 cm.

*Width.*—About 2 cm.

*Shape.*—Narrowly elliptic.

*Apex.*—Acute.

*Base.*—Obtuse.

*Margin.*—Entire.

*Texture, upper and lower surfaces.*—Sparsely pubescent.

*Venation pattern.*—Pinnate; reticulate.

Color.—Developing leaves, upper surface: Close to 143A. Developing leaves, lower surface: Close to 137C. Fully expanded leaves, upper surface: Close to 137A; venation, close to 145D. Fully expanded leaves, lower surface: Close to 137C; venation, close to 145D.

*Petiole.*—Length: About 3.4 mm. Diameter: About 1.4 mm. Texture, upper and lower surfaces: Sparsely pubescent. Color, upper and lower surfaces: Close to 145D.

Flower description:

*Flower arrangement and habit.*—Single salverform flowers arising from upper leaf axils. Freely flowering habit with usually about 22 flowers per plant at one time. Flowers face upright or outwardly.

*Fragrance.*—Not detected.

*Natural flowering season.*—Long flowering period; flowering commences naturally during the spring and plants flower continuously throughout the summer until late autumn in Japan.

*Flower longevity.*—Individual flowers last about two to three days on the plant. Flowers not persistent.

*Flower diameter.*—About 5.6 cm.

*Flower length (depth).*—About 3.1 cm.

*Throat diameter.*—About 1.7 mm.

*Tube length.*—About 3 cm.

*Tube diameter, at the base.*—About 1.4 mm.

*Flower bud.*—Shape: Cylindrical. Length: About 3.5 cm. Diameter: About 3.6 mm. Color: Close to 56D.

*Corolla.*—Arrangement: Five petals fused at the base and flaring outwardly forming a star-shaped flower. Petal length from throat: About 3 cm. Petal width: About 2.1 cm. Petal shape: Obovate. Petal apex: Mucronate. Petal base: Attenuate. Petal margin: Entire. Petal texture, upper and lower surfaces: Smooth, glabrous; velvety. Throat texture: Smooth, glabrous. Tube texture: Sparsely pubescent. Color: Petal, when opening and fully opened, upper surface: Close to N66C; "eye", close to 60B. Color becoming closer to N66D with development. Petal, when opening and fully opened, lower surface: Close to N155B. Throat: Close to 145C. Tube: Close to 145C.

*Calyx.*—Arrangement: One star-shaped calyx tube with five sepals fused at the base per flower. Sepal length: About 4.3 mm. Sepal width: About 1.3 mm. Sepal shape: Lanceolate. Sepal apex: Acute. Sepal margin: Entire. Sepal texture, upper and lower surfaces: Sparsely pubescent. Color, immature and mature, upper surface: Close to 143A. Color, immature and mature, lower surface: Close to 143A.

*Peduncles.*—Length: About 3 mm. Diameter: About 1.5 mm. Angle: Upright to outward. Strength: Strong. Texture: Smooth, glabrous. Color: Close to 145B.

*Reproductive organs.*—Stamens: Quantity/arrangement: Five per flower. Stamen length: About 2.6 mm. Anther shape: Narrowly elliptic. Anther size: About 2.7 mm by 1.3 mm. Anther color: Close to 154C. Pollen amount: Moderate. Pollen color: Close to 1D. Pistils: Quantity: One per flower. Pistil length: About 2.5 cm. Style color: Close to 145D. Stigma shape: Transversely ellipsoidal. Stigma color: Close to 145A. Ovary color: Close to 145A. Seed/fruit: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen/pest resistance: Plants of the new *Catharanthus* have not been observed to be resistant to pests and pathogens common to *Catharanthus*.

It is claimed:

1. A new and distinct *Catharanthus* plant named 'Sunnichipink' as illustrated and described.

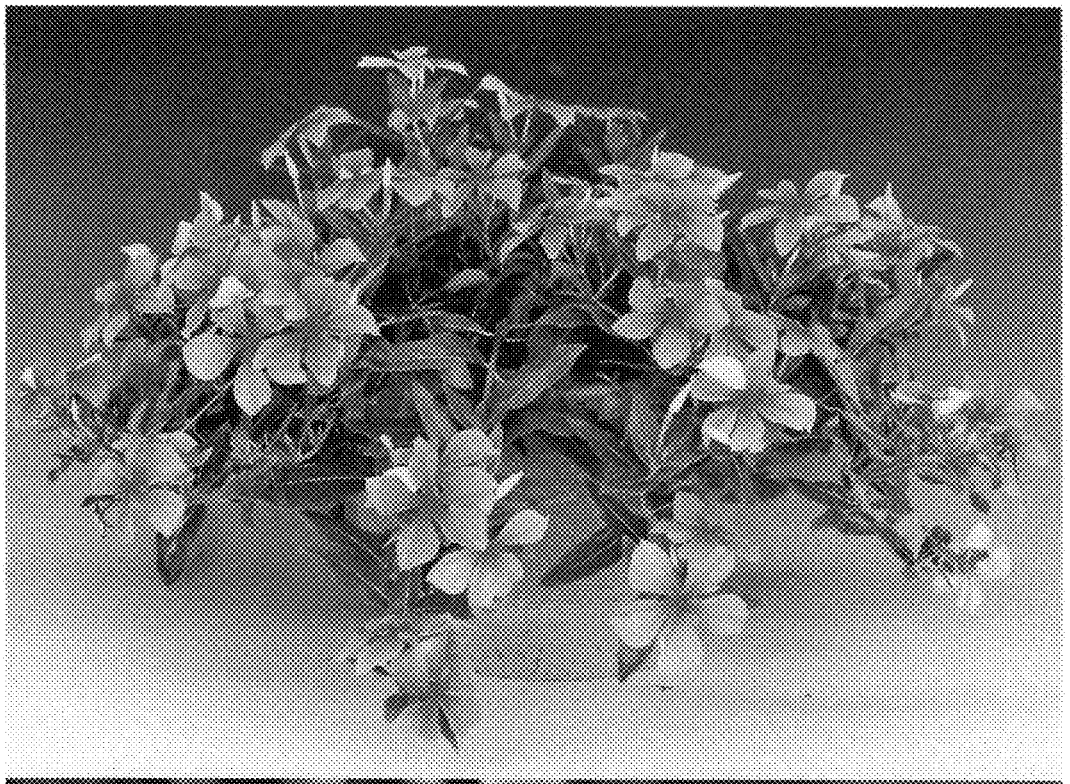
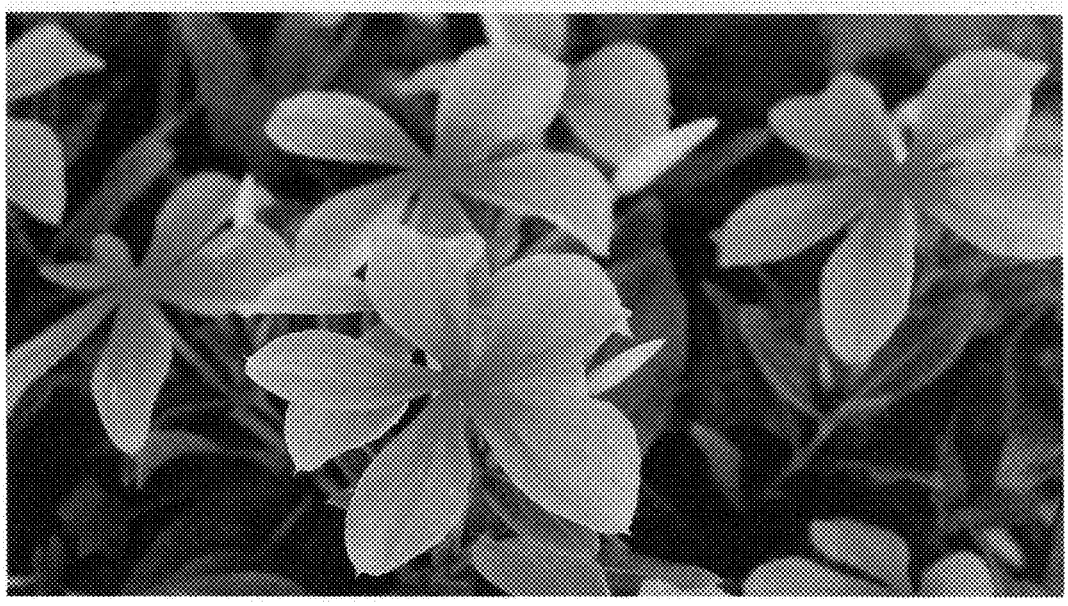

* * * * *